US008512747B2

(12) United States Patent
Pettersson et al.

(10) Patent No.: US 8,512,747 B2
(45) Date of Patent: *Aug. 20, 2013

(54) PHARMACEUTICAL COMPOSITION FOR THE TREATMENT OF ACUTE DISORDERS

(75) Inventors: Anders Pettersson, Kode (SE); Christer Nystrom, Lidingo (SE)

(73) Assignee: Orexo AB, Uppsala (SE)

( * ) Notice: Subject to any disclaimer, the term of this patent is extended or adjusted under 35 U.S.C. 154(b) by 0 days.

This patent is subject to a terminal disclaimer.

(21) Appl. No.: 13/302,720

(22) Filed: Nov. 22, 2011

(65) Prior Publication Data

US 2012/0315331 A1 Dec. 13, 2012

Related U.S. Application Data

(60) Continuation-in-part of application No. 12/216,197, filed on Jul. 1, 2008, now abandoned, which is a division of application No. 10/851,215, filed on May 24, 2004, now abandoned, which is a continuation of application No. 09/787,888, filed as application No. PCT/SE99/01687 on Sep. 24, 1999, now Pat. No. 6,761,910.

(30) Foreign Application Priority Data

Sep. 24, 1998 (SE) ........................................ 9803240

(51) Int. Cl.
*A61K 9/14* (2006.01)
*A61K 9/26* (2006.01)

(52) U.S. Cl.
USPC ............ 424/465; 424/472; 424/479; 424/489

(58) Field of Classification Search
USPC .................................................. 424/465–489
See application file for complete search history.

(56) References Cited

U.S. PATENT DOCUMENTS

| | | |
|---|---|---|
| 4,206,209 A | 6/1980 | Kracauer et al. |
| 4,229,447 A | 10/1980 | Porter |
| 4,371,516 A | 2/1983 | Gregory et al. |
| 4,432,975 A | 2/1984 | Libby |
| 4,574,080 A | 3/1986 | Roswall et al. |
| 4,582,835 A | 4/1986 | Lewis et al. |
| 4,755,389 A | 7/1988 | Jones et al. |
| 4,866,046 A | 9/1989 | Amer |
| 5,047,244 A | 9/1991 | Sanvordeker et al. |
| 5,112,616 A | 5/1992 | McCarty |
| 5,288,497 A | 2/1994 | Stanley et al. |
| 5,288,498 A | 2/1994 | Stanley et al. |
| 5,290,561 A | 3/1994 | Farhadieh et al. |
| 5,370,862 A | 12/1994 | Klokkers-Bethke et al. |
| 5,719,197 A | 2/1998 | Kanios et al. |
| 5,733,571 A | 3/1998 | Sackler |
| 5,747,494 A * | 5/1998 | Medjad et al. ............ 514/255.04 |
| 5,762,961 A | 6/1998 | Roser et al. |
| 5,948,389 A | 9/1999 | Stein |
| 5,968,547 A | 10/1999 | Reder et al. |
| 6,074,670 A * | 6/2000 | Stamm et al. ................. 424/462 |
| 6,264,974 B1 | 7/2001 | Madhat |
| 6,309,668 B1 * | 10/2001 | Bastin et al. .................. 424/472 |
| 6,514,531 B1 | 2/2003 | Alaux et al. |
| 6,638,535 B2 | 10/2003 | Lemmens et al. |
| 6,759,059 B1 | 7/2004 | Pettersson et al. |
| 6,761,910 B1 | 7/2004 | Pettersson et al. |
| 6,974,590 B2 | 12/2005 | Pather et al. |

FOREIGN PATENT DOCUMENTS

| | | |
|---|---|---|
| AU | 746373 B2 | 4/2002 |
| CA | 2274893 A1 | 6/1998 |
| CN | 1290525 A | 4/2001 |
| CN | 1418631 A | 5/2003 |
| EP | 0144243 A1 | 6/1985 |
| EP | 0324725 A1 | 7/1989 |
| EP | 1260216 A1 | 11/2002 |
| JP | 60-146824 A | 8/1985 |
| JP | 06-065103 A | 3/1994 |
| JP | H08-500578 A | 1/1996 |
| JP | H08-504189 A | 5/1996 |
| WO | WO-90/04962 A1 | 5/1990 |
| WO | WO-94/03186 A1 | 2/1994 |
| WO | WO-94/06426 A1 | 3/1994 |
| WO | WO-95/01782 A2 | 1/1995 |
| WO | WO-97/15297 A1 | 5/1997 |
| WO | WO-98/26763 A1 | 6/1998 |
| WO | WO-99/24023 A2 | 5/1999 |
| WO | WO-99/36071 A1 | 7/1999 |
| WO | WO-00/16750 A1 | 3/2000 |

(Continued)

OTHER PUBLICATIONS

Arky et al., Physicians' Desk Reference, 52nd Edition, pp. 2613-2615 (1998).

(Continued)

*Primary Examiner* — Michael G Hartley
*Assistant Examiner* — Micah-Paul Young
(74) *Attorney, Agent, or Firm* — Covington & Burling LLP

(57) ABSTRACT

A pharmaceutical composition for the treatment of acute disorders is described. The composition comprises an essentially water-free, ordered mixture of at least one pharmaceutically active agent in the form of microparticles which are adhered to the surfaces of carrier particles which are substantially larger than the particles of the active agent or agents, and are essentially water-soluble, in combination with the bioadhesion and/or mucoadhesion promoting agent. The invention also relates to a method for preparing the composition and to the use of the composition for the treatment of acute disorders.

4 Claims, 1 Drawing Sheet

(56) References Cited

FOREIGN PATENT DOCUMENTS

| | | |
|---|---|---|
| WO | WO-00/33835 A1 | 6/2000 |
| WO | WO-01/30391 A2 | 5/2001 |
| WO | WO-03/059349 A1 | 7/2003 |
| WO | WO-2004/091585 A1 | 10/2004 |

OTHER PUBLICATIONS

Ashburn et al., Oral transmucosal fentanyl citrate for the treatment of breakthrough cancer pain: a case report, Anesthesiology, 71: 615-17 (1989).

Ativan® Trade Literature, Copyright 1996-2005.

Bernards, Opiodids in pain control, basic and clinical aspects, p. 171 (1999).

British National Formulary, vol. 48, pp. 174-175, Sep. 2004.

Ciraulo et al., Pharmacokinetics and pharmacodynamics of multiple sublingual buprenorphine tablets in dose-escalation trials, Journal of Clinical Pharmacology 46:179-192 (2006).

Collett et al., Modified-release peroral dosage forms, Pharmaceutics: The Science of Dosage Form Design, Chapter 20, pp. 289-306 at p. 303 (2002).

Darcourt et al., The safety and tolerability of zolpidem—an update. Journal of Psychopharmacology, 13(1): 81-93 (1999).

Drover et al., Pharmacokinetics, pharmacodynamics, and relative pharmacokinetic/pharmacodynamic profiles of zalepion and zolpide, Clinical Therapeutics, vol. 22, No. 12 (2000).

Duchene et al., Bioadhesion of solid oral dosage forms, why and how?, Eur. J. Pharm. Biopharm., 44:15-23 (1997).

Farrar et al., Oral transmucosal fentanyl citrate: randomized, double-blinded, placebo-controlled trial for treatment of breakthrough pain in cancer patients, J. Natl. Cancer Inst. (United States), vol. 90, No. 8, pp. 611-616 (1998).

Fine et al., An open label study of oral transmucosal fentanyl citrate (OTFC) for the treatment of breakthrough cancer pain, Pain, 45: 149-53 (1991).

Gaserod et al., The enhancement of the bioadhesive properties of calcium alginate gel beads by coating with chitosan, Intl. J. Pharm. 195: 237-46 (1998).

Guidance for Industry: Labelling Guidance for Zolpidem Tablets, U.S. Dept. of Health and Human Services (1997).

Harris, Opportunities provided by the buccal and nasal administration of peptides, Minutes European Symposium on Buccal and Nasal Administration as an Alternative to Parenteral Administration. Paris, France, Dec. 10-11, 1991, pp. 204-255.

Holm et al., An update of its pharmacology, therapeutic efficacy and tolerability in the treatment of insomnia, Drugs, 59(4): 865-89 (2000).

Kroboth et al., Triazolam pharmacokinetics after intravenous, oral, and sublingual administration, Journal of Clinical Psychopharmacology, vol. 15, pp. 259-262 (1995).

Kunz et al., Severe episodic pain: management with sublingual sufentanil, Journal of Pain and Symptom Management, vol. 8, No. 4, pp. 189-190 (1993).

Lennernäs et al., Pharmacokinetics and tolerability of different doses of fentanyl following sublingual administration of a rapidly dissolving tablet to cancer patients: a new approach to treatment of incident pain, British Journal of Clinical Pharmacology 59(2): 249-53 (2005).

Leung et al., Polyanionic polymers in bio-and mucoadhesive drug delivery, polyelectrolyte gels, American Chemical Society, pp. 269-284 (1992).

Lieberman et al., Sustained release through coating, Pharmaceutical Dosage Forms, pp. 185-187 (1982).

Litigation Contentions Relating to US 6,761,910 Disclosed by Edict Pharmaceutical PUT, LTD., 2011.

Malmqvist et al., Studies on direct compression of tablets, IX: The effect of scaling-up on the preparation of ordered mixtures in double-cone mixers, Acta pharmaceutica suecica 21: 21-30 (1984).

Mashkovsky, Meditsina, Medicaments, Moscow, Part 1, pp. 175-176 (1985).

Mather, Clinical pharmacokinetics of fentanyl and its newer derivatives; Clinical Pharmacokinetics 8: 422-46 (1983).

Nyström et al., The use of ordered mixtures for improving the dissolution rate of low solubility compounds, J. Pharm. Pharmacol, 38: 161-65 (1986).

Office Action mailed Jan. 14, 2011 in U.S. Appl. No. 11/666,361.

Rowland et al., Clinical Pharmacokinetics Concepts and Applications, pp. 110-130 (1995).

Salva et al., Clinical pharmacokinetics and pharmacodynamics of zolpidem, Clin. Pharmacokinet., 29(3): 142-53 (1995).

Shojaei, Buccal mucosa as a route for systemic drug delivery: a review, J. Pharm. Pharmaceut. Sci., 1(1): 15-30 (1998).

Stanley et al., Novel delivery systems: oral transmucosal and intranasal transmucosal, Journal of Pain and Symptom Management, vol. 7 No. 3 (1992).

Stanley et al., Oral transmucosal fentanyl citrate (lollipop) premedication in human volunteers, Anesth. Analog. 69: 21-27 (1989).

Taylan et al., Design and evaluation of sustained-release and buccal adhesive propranolol hydrochloride tablets, Journal of Controlled Release 38: 11-20 (1996).

Terzano et al. New drugs for insomnia, Surg. Safety, 26(4): 261-82 (2003).

The Lecture of Pharmacology, 2: 236, Mar. 20, 1987.

Vogt et al., Pharmacokinetics and haemodynamic effects of ISDN following different dosage forms and routes of administration, Eur. J. Clin. Pharmacol. 46: 319-24 (1994).

Voorspoels et al., Buccal absorption of testosterone and its esters using a bioadhesive tablet in dogs, Pharmaceutical Research 13 (8): 1228-32 (1996).

Website: www.rxlist.com/duragesic-drug.htm; Duragesic (Fentanyl Transdermal) Drug Information: Uses, Side Effects, Drug Interactions, Apr. 23, 2009.

Weinberg et al., Sublingual absorption of selected opioid analgesics, Clinical Pharmacology and Therapeutics 44(3): 335-42 (1988).

Westerberg et al., Physicochemical aspects of drug release XVIII. the use of a surfactant and a disintegrant for improving drug dissolution rate from ordered mixtures, S.T.P. Pharma Sci. 3(2): 142-47 (1993).

International Search Report dated Jan. 22, 2000 issued in International Application No. PCT/SE99/01687.

\* cited by examiner

PHARMACEUTICAL COMPOSITION FOR THE TREATMENT OF ACUTE DISORDERS

RELATED APPLICATIONS

This application is a continuation-in-part of co-pending U.S. patent application Ser. No. 12/216,197, filed on Jul. 1, 2008 and entitled "Pharmaceutical Composition for the Treatment of Acute Disorders," which is a divisional of U.S. patent application Ser. No. 10/851,215, filed on May 24, 2004, which is a continuation of U.S. patent application Ser. No. 09/787,888, filed on Jun. 8, 2001 (now U.S. Pat. No. 6,761,910), which is the national phase of PCT International Application No. PCT/SE99/01687, filed on Sep. 24, 1999 under 35 U.S.C. §371, which claims the priority benefit of Sweden Patent Application No. 9803240-2, filed on Sep. 24, 1998 under 35 U.S.C. §119, the entire contents of each are incorporated herein by reference.

FIELD OF THE INVENTION

The present invention relates to a rapidly acting pharmaceutical composition for sublingual administration of a pharmaceutical agent, to a method for preparing such a composition, and to a method for the treatment of acute disorders by the use of such a composition.

BACKGROUND OF THE INVENTION

Acute and/or severe disorders are a common cause of emergency treatment or hospitalization. One of the most common disorders of this type is acute or breakthrough pain. In cancer patients, pain is usually treated with non-steroid anti-inflammatory drugs (NSAIDs) and opiates alone or in combination. Opioid-requiring cancer pain patients are usually given slow-release opiates (slow-release morphine or ketobemidone or transdermal fentanyl). A characteristic feature of cancer pain are periods of inadequate analgesia (breakthrough pain). Most often they are due to increased physical activity of the patient. However, treatment of breakthrough pain by administration of increased time contingent doses of long-acting analgesics causes adverse side effects such as excess sedation, nausea, and constipation.

Other disorders and conditions which require a fast-acting treatment are, for example, pulmonary edema, gastroesophageal reflux, insomnia and nephrolitiasis.

Presently available oral, rectal, or sublingual formulations have relatively lengthy onset times or erratic absorption characteristics that are not well suited to control acute disorders.

Conditions of acute operative/postoperative or traumatic/posttraumatic pain as well as pain due to severe disease (e.g. myocardial infarction, nephrolithiasis, etc.) is usually treated with opioid analgesics which are administered parenterally (by intravenous or intramuscular administration) to obtain a rapid onset of analgesia. In such cases, rapid-onset oral alternatives are of considerable therapeutic interest. Also for the treatment of other acute disorders, it is of considerable interest to provide fast-acting therapeutic compositions which may be administered orally instead of parenterally or rectally.

However, many pharmaceutically active agents which would be advantageous to administer orally are not suitable to be swallowed. They may, for example, be inactivated by the gastrointestinal liquids, have a slow action because of a low solubility in the aqueous medium, or be highly susceptible to metabolism by gastro-intestinal enzymes and have poor absorption properties, as exemplified for peptide hormones. It is therefore more preferable to arrange for the active component to be taken up through the mucous membranes of the oral cavity. Here, the most preferred way of administration is via the sublingual route. In this administration, a dosage unit of the pharmaceutical composition is placed under the tongue, and the active component is absorbed through the surrounding mucous membranes. However, with this way of administration, the risk that the patient swallows the medication by swallowing saliva is well known.

For the treatment of acute pain fentanyl, N-(1-phenethyl-4-piperidyl) propioanilide, or one of its pharmaceutically acceptable salts may be used. This compound is an opioid agonist and shares many of the pharmacodynamic effects of opiates such as morphine and meperidine. However, compared to these opiates, fentanyl exhibits little hypnotic activity, rarely induces histamine release, and respiratory depression is more short-lived. Fentanyl is commercially available for intravenous, intrabucchal (lozenge-transmucosal) and transdermal administration.

Following parenteral administration of fentanyl, the analgesic action is more prompt and less prolonged than that of morphine and meperidine. The onset of analgesia following i.v. administration is rapid. Peak analgesia is obtained within a few minutes. Following transbuccal administration by a lozenge, consumption of the lozenge is usually complete within 30 min and peak plasma concentrations appear after around 20 minutes, as described by e.g. Farrar et al., J. Natl. Cancer Inst., 1998, 90(8), p. 611-616. Analgesia is apparent within 5-15 min and peaks at about 20-50 min. While this is an improvement over oral administration for gastrointestinal uptake, a quicker onset of analgesia would be of substantial benefit to the patient. In addition, substantial amounts of lozenge-administered fentanyl are swallowed by the patient. This is not desirable and results in the administration of excessive amounts of the drug, which may give rise to side effects.

OBJECTS OF THE INVENTION

It is one object of the invention to provide for the treatment of acute disorders by perorally administering at least one pharmaceutically active agent in a manner giving rise to pharmacologically effective plasma levels of said agent or agents within a short time after administration.

It is another object of the invention to provide a pharmaceutical composition suitable for that purpose.

It is a further object of the invention to provide a method of making such a composition. It is an additional object of the invention to provide a method of manufacture of a medicament for sublingual administration containing a physiologically effective dose of at least one pharmaceutically active compound useful in the treatment of acute disorders.

SUMMARY OF THE INVENTION

Figure 1:
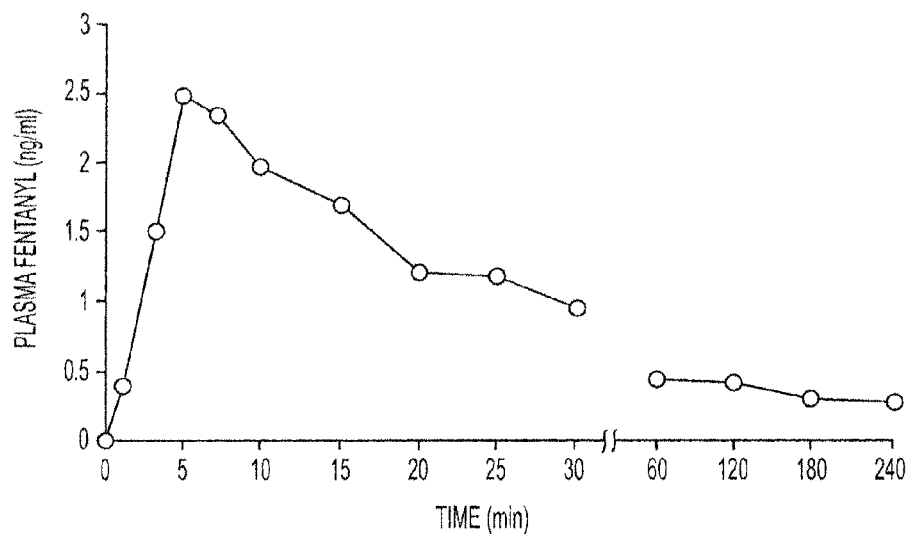
FIG. 1 is an illustration of a plasma concentration-time profile, which may be obtained for an active agent over time, if administered in a composition according to the invention, as described in Example 3.

According to the invention, the peroral treatment of acute disorders comprises sublingual administration of an ordered mixture comprising a pharmacologically effective amount of at least one pharmaceutically active agent. Said agent or agents is administered sublingually in combination with a bioadhesion and/or mucoadhesion promoting compound.

Further according to the invention, there is also provided a single-dose pharmaceutical composition for sublingual administration, comprising a pharmacologically effective amount of at least one pharmaceutically active agent. Said composition also contains a bioadhesion or mucoadhesion promoting compound. This composition reduces erratic drug absorption via swallowed saliva and enables the administration of small amounts of said agent or agents. Therefore, it substantially reduces the risk of side effects and intrapatient as well as interpatient variation of therapeutic response. Thereby the risk of drug accumulation is reduced, making the pharmaceutical preparation well suited for repeated dosing in patients suffering from acute disorders.

The amount of active agent or agents contained in the pharmaceutical composition of the invention is obviously dependent on a number of factors, which are to be evaluated by the treating physician. Among such factors may be mentioned the specific agent used and the type of disorder being treated, the medical status of the patient, and others.

When fentanyl is used for the treatment of acute or breakthrough pain, the composition of the invention should contain from 0.05 up to 20 weight percent of fentanyl or one of its pharmaceutically acceptable salts. More preferably, the compositions contain from 0.05 to 5 weight percent of fentanyl, and especially from 0.1 to 1 weight percent. The contents can also be expressed as the amount of fentanyl in a dose unit of the composition, such as a tablet. In this case, a dose unit should contain from 0.05 to 20 mg, and preferably 0.1 to 5 mg of fentanyl. When the fentanyl is used in the form of a salt, these percentages and amounts should be recalculated accordingly.

Still further according to the invention, the sublingual composition comprises an ordered mixture of one or more bioadhesive and/or mucoadhesive carrier substances coated with the pharmaceutically active agent or agents in a fine particulate form.

It is preferred to formulate the composition according to the invention by use of the technology for formulating rapidly dissolving ordered-mixture compositions disclosed in European patent EP 0324 725. In these compositions, the drug in a finely dispersed state covers the surface of substantially larger carrier particles. Such compositions disintegrate rapidly in water, thereby dispersing their contents of microscopic drug particles.

However, this prior art technique of using an ordered mixture for rapid drug dissolution has hitherto only been reported to be suitable for conventional oral drug therapy, i.e. for solid dosage forms which are to be swallowed. For such preparations, the dissolution of the drug particles takes place in the stomach, i.e. in an environment where there exists a relatively large volume of liquid which can dissolve the drug particles. In the entire prior art literature, dissolution testing of ordered mixtures has been conducted with a large volume of water, typically 1 liter. The possibility to use ordered mixtures for sublingual administration, where the volume of liquid available as a solvent is limited to a few milliliters, has not been considered as a feasible approach. It was therefore unexpected that the present form of a solid dosage form preparation and administration route gives positive and useful results.

In such an ordered mixture, the active agent or agents have a mean particle size below 10 μm. This size is determined on a weight basis, as obtained directly by e.g. dry sieving analysis, as is known by those skilled in the art.

A bioadhesion and/or mucoadhesion promoting agent is additionally added to the carrier particles according to the invention. The bioadhesion and/or mucoadhesion promoting agent is effective in making the active agent or agents adhere to the oral mucosa and may, in addition, possess properties to swell and expand in contact with water and thus make the tablet or the carrier particles disintegrate when wetted with saliva. The bio/mucoadhesion promoting agent must then be present on the surface of the carrier particles, but it may optionally also be present within these particles, as described below.

The expression "mucoadhesion" is meant to denote an adhesion to mucous membranes which are covered by mucus, such as those in the oral cavity, while the expression "bioadhesion" is meant to denote an adhesion to biological surfaces more in general, including mucous membranes which are not covered by mucus. These expressions generally overlap as definitions, and may usually be used interchangeably, although the expression "bioadhesive" has a somewhat wider scope. In the present specification and claims, the two expressions serve the same purpose as regards the objects of the invention, and this has been expressed by the use of the common term "bio/mucoadhesion".

Suitably the carrier particles contain from 0.1 up to 25 weight percent of bio/mucoadhesion promoting compound, based on the total composition. In practice, contents below 1 weight percent have been found to give an insufficient bio/mucoadhesive effect. The preferred range of bio/mucoadhesion promoting agent content is from 1 to 15 weight percent.

It is preferred that the bio/mucoadhesion promoting agent is a polymeric substance, preferably a substance with an average molecular weight above 5,000 (weight average). The level of hydration of the mucosa adhesion promoting agent interface is of importance in the development of bio/mucoadhesive forces. Therefore, the faster the swelling of the polymer, the faster is the initiation of bio/mucoadhesion. The hydration of bioadhesive compounds also makes them useful as absorption enhancers according to the invention.

Preferably, the carrier particle size is from 50 to 750 μm, and more preferredly from 100 to 600 μm. Although particle sizes outside the indicated range can be used, practical difficulties are experienced when formulating pharmaceutical preparations from particles having such sizes. The carrier used may comprise any substance which is pharmaceutically acceptable, is highly soluble in water, and which can be formulated into particles fit for incorporating a bio/mucoadhesion promoting agent. A number of such substances are known to the person skilled in this art. As suitable examples may be mentioned carbohydrates, such as sugar, mannitol and lactose, or pharmaceutically acceptable inorganic salts, such as sodium chloride or calcium phosphate.

In accordance with one particularly preferred aspect of the invention, the carrier also comprises a fragmentation promoting agent. By a fragmentation promoting agent is meant a brittle material which is readily crushed or broken up when a pharmaceutical composition of which it forms a part is compacted into tablets. If a bio/mucoadhesion promoting agent also is incorporated within the carrier as well as being added to the carrier surface, further surfaces of bio/mucoadhesion promoting agent may then be exposed for hydration. This effect is especially pronounced when the bio/mucoadhesion promoting agent also serves as a disintegrant. Mannitol and lactose have been found to be particularly suitable as fragmentation promoting agents.

The addition of a pharmaceutically acceptable surfactant to the composition is also a preferred feature of the invention. The increased wetting effect of the surfactant enhances the hydration of the carrier particles, which results in faster initiation of the bio/mucoadhesion. The surfactant should be in a finely dispersed form and intimately mixed with the active agent or agents. The amount of surfactant should be from 0.5 to 5 weight percent of the composition, and preferably then from 0.5 to 3 weight percent.

As examples of suitable surfactants may be mentioned sodium lauryl sulfate, polysorbates, bile acid salts and mixtures of these.

A variety of polymers known in the art can be used as bio/mucoadhesion promoting agents. In addition to their polymeric nature, their ability to swell is important. On the other hand, it is also important that they are substantially insoluble in water. Their swelling factor by volume when brought into contact with water or saliva should preferably be at least 10, while a factor of at least 20 is more preferred. Examples of such bio/mucoadhesion promoting agents include cellulose derivatives such as hydroxypropylmethyl cellulose (HPMC), hydroxyethyl cellulose (HEC), hydroxypropyl cellulose (HPC), methyl cellulose, ethyl hydroxyethyl cellulose, carboxymethyl cellulose and sodium carboxymethyl cellulose (NaCMC); starch derivatives such as moderately cross-linked starch; acrylic polymers such as carbomer and its derivatives (polycarbophyl, Carbopol®, etc.); polyethylene oxide (PEO); chitosan (poly-(D-glucosamine)); natural polymers such as gelatin, sodium alginate, pectin; scleroglucan; xanthan gum; guar gum; poly co-(methylvinyl ether/maleic anhydride); and crosscaramellose. Combinations of two or more bio/mucoadhesive polymers can also be used. More generally, any physiologically acceptable agent showing bio/mucoadhesive characteristics may be used successfully to be incorporated in the carrier. Bio/mucoadhesiveness can be determined in vitro, e.g. according to G. Sala et al., Proceed, Int. Symp. Contr. Release. Bioact. Mat. 16:420, 1989.

Some suitable commercial sources for representative bio/mucoadhesive polymers include:

Carbopol® acrylic copolymer—BF Goodrich Chemical Co, Cleveland, 08, USA;
HPMC—Dow Chemical Co., Midland, Mich., USA;
NEC (Natrosol)—Hercules Inc., Wilmington, Del., USA;
HPC (Klucel®)—Dow Chemical Co., Midland, Mich., USA;
NaCMC—Hercules Inc. Wilmington, Del., USA;
PEO—Aldrich Chemicals, USA;
Sodium Alginate,—Edward Mandell Co., Inc., Carmel, N.Y., USA;
Pectin—BF Goodrich Chemical Co., Cleveland, Ohio., USA.'
Ac-Di-Sol® (modified cellulose gum with a high swellability)—FMC Corp., USA;
Actigum,—Mero-Rausselot-Satia Baupte, France;
Satiaxane—Sanofi BioIndustries, Paris, France;
Gantrez®—ISP, Milan, Italy;
Chitosan—Sigma, St Louis, Mo., USA;

Depending on the type and the proportion of the bio/mucoadhesion promoting agent used, the rate and intensity of bio/mucoadhesion may be varied. According to one of the preferred aspects of the invention, substances with high and rapid capacity for swelling are preferred.

In order for the pharmaceutical composition of the invention to function properly when a bio/mucoadhesion promoting agent is added thereto, this agent must be positioned at the surfaces of the carrier particles. The bio/mucoadhesion promoting agent can then be admixed to the carrier particles in several ways. In a preferred embodiment of the invention, a fine particulate quality of the bio/mucoadhesion promoting agent is mixed together with the coarse carrier for a sufficient time to produce an ordered mixture, where the finer particles exist as discrete primary particles adhered to the surfaces of the carrier particles. Thus, the bio/mucoadhesion promoting agent is admixed in the same way as the active compound described in European patent No. 0 324 725.

In yet another embodiment of the invention, the bio/mucoadhesion promoting agent may, besides its peripheral orientation on the surfaces of the carrier particles, also be incorporated into the carrier particles in various ways. For example, the finely dispersed carrier can be granulated together with finely dispersed bio/mucoadhesive in a liquid which does not dissolve the bio/mucoadhesive agent or cause it to swell. In this case, the dry constituents are first mixed, and the resultant mix is then moistened with a non-dissolving/non-swelling liquid, such as absolute ethanol. The resultant mass is granulated, for instance by forcing it through a filter. It is then dried and finely ground. Alternatively, the moist mass can he dried and then granulated. Another way of producing the carrier particles according to the invention is by dissolving the carrier agent in a solvent which will not dissolve the bio/mucoadhesion promoting agent or cause it to swell, followed by the addition of the bio/mucoadhesion promoting agent to the solution, evaporation of the solvent, and granulation of the residue. Other methods are also conceivable to the person skilled in this art. Irrespective of the method applied, a suitable grain size fraction of the carrier agent containing bio/mucoadhesion promoting agent is prepared in a final stage, e.g. by passing the particulate mixtures through a screen or sieve of an appropriate mesh size, for instance a U.S. mesh size from 35 to 170.

The bio/mucoadhesion promoting agent suitably has a particle size between 1 and 100 μm. When the particles of this agent are to be mixed with the carrier particles to form an ordered mixture, their size lies within the lower part of the size interval, and suitably their size is then below 10 μm. When the bio/mucoadhesion promoting agent is to be incorporated in the carrier particles, its particle size may be within the upper part of the size interval.

The invention is particularly directed to the administration of drugs which are used for the treatment of medical conditions where a rapid and transient effect is desirable, such as pain, insomnia, allergic conditions and pulmonary edema. As non-limiting examples of such drugs may be mentioned morphine (analgetic), fentanyl (analgetic), alfentanyl (analgetic), sufentanyl (analgetic), buprenorphine (analgetic), pizotifen (analgetic), sumatriptan (analgetic), indomethacin (analgetic), sulindac (analgetic), diclofenac (analgetic), ketorolac (analgetic), piroxicam (analgetic), tenoxicanl (analgetic), ibuprofen (analgetic), naproxen (analgetic), ketoprofen (analgetic), butazolidine (analgetic), phenylbutazone (analgetic), diazepam (insomnia), oxazepam (insomnia), zopiclone (insomnia), zolpidem (insomnia), propiomazin (insomnia), valeriana (insomnia), levomepromazin (insomnia), cyclizine (allergy), cetirizine (allergy), terfenadine (allergy), acrivastine (allergy), fexofenadine (allergy) and furosemide (diuretic).

Other drugs which benefit from an enhanced absorption and which may be used for medical conditions where a rapid onset of the action is desirable include, without any limiting sense, various peptides and enzymes, such as atrial natriuretic peptides (ANP, ANF, auriculin) (diuretics), brain natriuretic peptides (diuretics), platelet aggregation inhibitors (anticoagulants), streptokinase (anticoagulant), heparin (anticoagulant), urokinase (anticoagulant), renin inhibitors (hypertension), insulin (antidiabetic), and sleep inducing peptide (insomnia).

Further examples of drugs where exposure to gastric acid has to be avoided and where the swallowing of active drug containing saliva can be minimized by means of the bio/mucoadhesive properties of the present formulations include, without any limiting sense, benzimidazole derivatives used as H+, K+ and ATPase inhibitors (gastric acid reduction), such as omeprazole, pantoprazole, perprazole and lansoprazole. Other H+, K+ and ATPase inhibitors include alyll isothiocyanate, trifluorperazide, nolinium bromide, RP 40749 and fenoctimine.

The invention is particularly suitable for the administration of fentanyl and its pharmacologically acceptable salts, such as the citrate or maleate, which are not readily soluble in water. The particles of fentanyl or salt thereof will suitably have a maximum particle size of about 24 μm but will preferably not be greater than about 10 μm. Fentanyl is caused to adhere to the carrier particles by dry mixing of the ingredients during a period of time of sufficient length. This time period can vary according to the mixing equipment used. A person skilled in the art will have no difficulty in determining by experimentation a suitable mixing time for a given combination of active substance, bio/mucoadhesion promoting agent and carrier, by using a particular mixing equipment.

Another preferred aspect of the invention comprises the incorporation of a disintegrating agent in the composition of the invention. Such an agent will accelerate the dispersion of the carrier particles. Examples of disintegrating agents according to the invention include cross-linked polyvinylpyrrolidone, carboxymethyl starch, natural starch, microcrystalline cellulose, cellulose gum and mixtures of these. A preferred content of disintegrating agent is from 1% to 10% of the composition. As can be seen, the definitions of the disintegrating agent and the bio/mucoadhesion promoting agent overlap somewhat, and it may be preferred that both functions are served by the same substance. However, it is important to note that these two categories of excipients are not equivalent, and there are efficiently functioning disintegrants which do not possess bio/mucoadhesive properties, and vice versa.

The ordered mixtures prepared in accordance with the present invention can be incorporated into various kinds of pharmaceutical preparations intended for sublingual administration. Irrespective of the form given to the preparation, it is important that the preparation is essentially free from water, since its bio/mucoadhesion promoting character results from its practically instantaneous hydration when brought into contact with water or saliva. Premature hydration would drastically decrease the mucoadhesion promoting properties and result in a premature dissolution of the active substance.

A pharmaceutical composition for the preferred sublingual route of administration can be obtained by combining an aforementioned ordered mixture with conventional pharmaceutical additives and excipients used in the art for sublingual preparations. Appropriate formulation methods are well known to the person skilled in the art; see, for instance, Pharmaceutical Dosage Forms: Tablets. Volume 1, 2nd Edition, Lieberman H A et al.; Eds.; Marcel Dekker, New York and Basel 1989, p. 354-356, and literature cited therein. Suitable additives comprise additional carrier agents, preservatives, lubricants, gliding agents, disintegrants, flavorings, and dyestuffs.

Thus, the invention provides a dosage form which is easy and inexpensive to manufacture, enables rapid active substance release, promotes a rapid uptake of the active agent or agents through the oral mucosa, and enhances the uptake of otherwise poorly soluble substances, such as peptides. The use of a low dose of active agent is provided for, supporting a short duration of action while enabling a repeated dosing schedule for patients in need of treatment of recurrent acute disorders.

The invention will now be illustrated in more detail by reference to examples showing preferred but not limiting embodiments.

EXAMPLE 1

Preparation of a Rapidly Disintegrating Tablet with Bio/Mucoadhesion Promoting Properties A batch of 1000 tablets is produced from the following composition: 81.5 g of mannitol and 2.0 g of Ac-Di-Sol® (disintegrant and bio/mucoadhesion promoting agent) is mixed with about 170 ml of absolute ethanol. The dried mixture is forced through a metal sieve of 1 mm mesh width and the resultant fraction, which has a particle size from about 250 to 450 microns, is mixed with 500 mg of micronized fentanyl and with 1.0 g of finely ground sodium lauryl sulfate (surfactant) over a period of 50 hours. The resulting mixture is admixed with 5.0 g of Avicel Ph 101 and 10.0 g sodium alginate (bio/mucoadhesion promoting agent and disintegrant) over a period of 60 minutes. If the resulting mixture is compacted into tablets at a compaction pressure of 200 MPa, each tablet has a weight of 100 mg and containing 0.5 mg of fentanyl.

If the tablets are thus produced, the dissolution rate of the tablets may be investigated in accordance with USP 30 XXIII (Paddle Method) at two different stirring speeds, 25 and 100 rpm.

EXAMPLE 2

Preparation of a Rapidly Disintegrating Tablet with Bio/Mucoadhesion Promoting Properties A batch of 1000 tablets is produced from the following composition: 91.0 g of mannitol (granular quality of a particle size from 250 to 450 μm) and 1.0 g of sodium lauryl sulfate and 500 mg of micronized fentanyl is mixed in a V-mixer over a period of 24 hours. Thereafter, 5.0 g of Avicel® PH101 and 2.0 g of Ac-Di-Sol® (which is used both as a disintegrant and as a bio/mucoadhesion promoting agent) is admixed for an additional 2 hours. Finally, 0.5 g of magnesium stearate is admixed for 2 minutes. If the resulting tablet mass is compacted into tablets at a compaction pressure of 130 MPa, each tablet contains 0.5 mg of fentanyl.

The disintegration time is tested with the use of the apparatus described in Ph.Eur. (latest edition), it is found that the disintegration time is less than 15 seconds.

For comparison, conventional rapidly dissolving tablets may also be produced. Dry mannitol having a particle size of 250-450 microns is dry mixed with micronized fentanyl without any further addition of excipients. The mixing time is 50 hours. If the resulting mixture is compacted into tablets at a compaction pressure of 200 MPa, each tablet will contain 0.5 mg of fentanyl.

If this investigation is made, the results will show that the ordered mixture with bio/mucoadhesive properties according to the invention has a dissolution rate equal to that of a conventional rapidly dissolving tablet formulation. If this investigation is made, the results will also show that the entire tablet is dissolved within 2 minutes. Furthermore, if this investigation is made, the results will show that the rapid disintegration found for the tablets of Example 2 is equal to or better than for the conventional tablets.

EXAMPLE 3

Evaluation of Uptake in Sublingual Administration

One patient suffering from breakthrough pain due to cancer is administered 400 μg of fentanyl as a sublingual tablet formulated as described in Example 1, and the plasma concentration of fentanyl is monitored for a time of 240 minutes after the administration, the results shown in the accompanying FIG. 1 are seen. It will be seen that the uptake of fentanyl is rapid. A sublingual preparation according to the invention gives a rapid uptake of the active agent, even though a very small volume of liquid is available for dissolution in this route of administration.

EXAMPLE 4

Evaluation of Bio/Mucoadhesive Properties

For in vitro evaluation of the bio/mucoadhesive properties of the formulation according to the present invention, a method permitting evaluation of bio/mucoadhesion promoting properties directly on finished dosage forms (Sala, G. E. et al., Proc. Int. Symp. Contr. Release Bioact. Mat. 16:420, 1989) is used. The evaluation is based on measurements of the flow of water required to remove the active substance from a rabbit intestinal membrane. A strip of rabbit mucosa is placed horizontally in a suitable temperature controlled chamber set at 37° C. The tissue is first washed with predetermined volumes of water by means of a peristaltic pump. Pre-compressed compositions according to Example 1 (5-15 mg) is then placed on the tissue and allowed to remain there for 2 minutes to ensure proper dissolution. Upon this an elution is followed with water fed by a peristaltic pump during 10 minutes. Rinsed-off fentanyl is collected, and its amount is determined by radioimmunoassay (RIA) in order to establish the percentage of fentanyl removed. Subsequent tests are carried out using increasing elution flow rates. If the evaluation is made, the results in Table 2 are seen, where percentages of removal at a high flow rate are listed for:

A Bio/mucoadhesive mixture according to the invention (Example 1);

B Bio/mucoadhesive mixture according to the invention (Example 2);

Conventional mixture for rapid dissolution containing no bio/mucoadhesion promoting agent.

TABLE 2

| Flow rate | % fentanyl removed | | |
|---|---|---|---|
| (ml/min) | A | B | C |
| >15 | <50 | <50 | >95 |

EXAMPLE 5

Preparation of Rapidly Disintegrating Tablets for the Administration of Furosemide Rapidly disintegrating tablets with bio/mucoadhesive properties for sublingual administration is prepared according to Example 1, with each tablet containing 20 mg of furosemide. The tablets show a rapid release of furosemide and a promoted uptake of furosemide through the oral mucosa in comparison with conventional peroral formulations. The preparation may be used for the treatment of pulmonary edema.

EXAMPLE 6

Preparation of Rapidly Disintegrating Tablets for the Administration of Atrial Natriuretic Peptide (ANP)

Rapidly disintegrating tablets with bio/mucoadhesive properties which in addition enhance absorption of large molecules in sublingual administration is prepared according to Example 1, with each tablet containing 0.7 mg ANP. The tablets show a rapid release of ANP and an enhanced uptake of ANP through the oral mucosa in comparison with conventional peroral formulations. The preparation may be used for the treatment of pulmonary edema.

EXAMPLE 7

Preparation of Rapidly Disintegrating Tablets for the Administration of Omeprazole Rapidly disintegrating tablets with bio/mucoadhesive properties for sublingual administration is prepared according to Example 1, with each tablet containing 10 mg of omeprazole. The tablets show a rapid release of omeprazole and an enhanced uptake of omeprazole through the oral mucosa, as well as a reduced swallowing of omeprazole in the saliva, in comparison with conventional peroral formulations. The preparation may be used for the treatment of gastroesophageal reflux.

EXAMPLE 8

Preparation of Rapidly Disintegrating Tablets for the Administration of Diclofenac Rapidly disintegrating tablets with bio/mucoadhesive properties for sublingual administration is prepared according to Example 1, with each tablet containing 50 mg of diclofenac. The tablets show a rapid release of diclofenac and an enhanced uptake of diclofenac through the oral mucosa in comparison with conventional peroral formulations. The preparation may be used for the treatment of painful conditions such as neprolithiasis.

EXAMPLE 9

Clinical Evaluation of Sublingual Tablet System for Rapid Oromucosal Absorption Using Fentanyl Citrate as the Active Substance Materials Micronised fentanyl citrate was employed as active ingredient. Granulated mannitol was used as carrier material, cross-linked polyvinylpyrrolidone and croscarmellose sodium (Ac-Di-Sol®) were used as disintegrant and bioadhesive components, silicified microcrystalline cellulose (Pro-Solv SMCC® 90) was used as a binder, citric acid was milled in a ball mill and was used in one of the formulations as an antioxidant, and magnesium stearate was used as a lubricant. All were used as supplied.

Preparation of Materials

Four batches of 120,000 fentanyl tablets (each with 400 μg doses of fentanyl base) were prepared as follows:

Firstly, in each case, fentanyl citrate (77.2872 g) and mannitol (7.0752 kg) were mixed together in a double-cone blender at 47 rpm for 10 hours.

Then, the following were added to the mixture:
(A) silicified microcrystalline cellulose (1.122 kg) and croscaramellose sodium (87.6 g);
(B) silicified microcrystalline cellulose (1.122 kg) and cross-linked polyvinylpyrrolidone (216 g);
(C) silicified microcrystalline cellulose (1.122 kg) and cross-linked polyvinylpyrrolidone (216 g), along with citric acid (25.68 g); and
(D) silicified microcrystalline cellulose (1.840 kg) and cross-linked polyvinylpyrrolidone (360 g).

Mixing was continued at 47 rpm for an additional 30 minutes.

Compaction of Tablets

Prior to compaction, all tablet masses were mixed with magnesium stearate (ca. 0.5% (w/w)) in a double-cone blender at 47 rpm for 2 min. Tablets were made in a rotary tablet press equipped with eight 6 mm flat bevel edged punches; the powder was filled into the die with a feed shoe. Each batch comprised 120,000 tablets.

Clinical Study

Study Design: An open randomized four-period crossover study to assess the bioavailability of sublingual fentanyl. The study was carried out at Quintiles Hermelinen, Varvsgatan 53, SE-972 33 Luleå, Sweden. This was a single-centre, open, randomized, four-period crossover trial to evaluate and compare the bioavailability of pharmaceutical compositions of sublingual fentanyl 400 μg.

The administrations of the four investigational products were given to the subjects in random order. The administrations were separated by a washout period of at least two days. To protect subjects from opioid-related adverse effects, the opioid antagonist naltrexone hydrochloride was administered 12 hours before each study drug administration.

Sixteen subjects (healthy male volunteer subjects between 18 and 45 years of age) were enrolled in the study and all subjects were analysed for safety and equivalence.

Adverse events (AEs) were monitored, as were haematology, clinical chemistry and urinalysis.

The primary variable ($AUC_{0-t}$) and the secondary variables ($AUC_{0-\infty}$, $C_{max}$, $t_{max}$, $C_{first}$, $t_{first}$ and $t_{1/2}$) were compared between treatments using the SAS statistical program PROC GLM with sequence, subject nested within sequence, period and treatment as class variables. Differences between treatments were given as 90% confidence intervals (CIs). Equivalence was proven if the 90% CI≦±20% (or the ratio was within 0.80-1.25 for AUC and 0.75-1.33 for $C_{max}$). Differences between treatments in outcome variables were tested at the 5% level.

Figure 2:
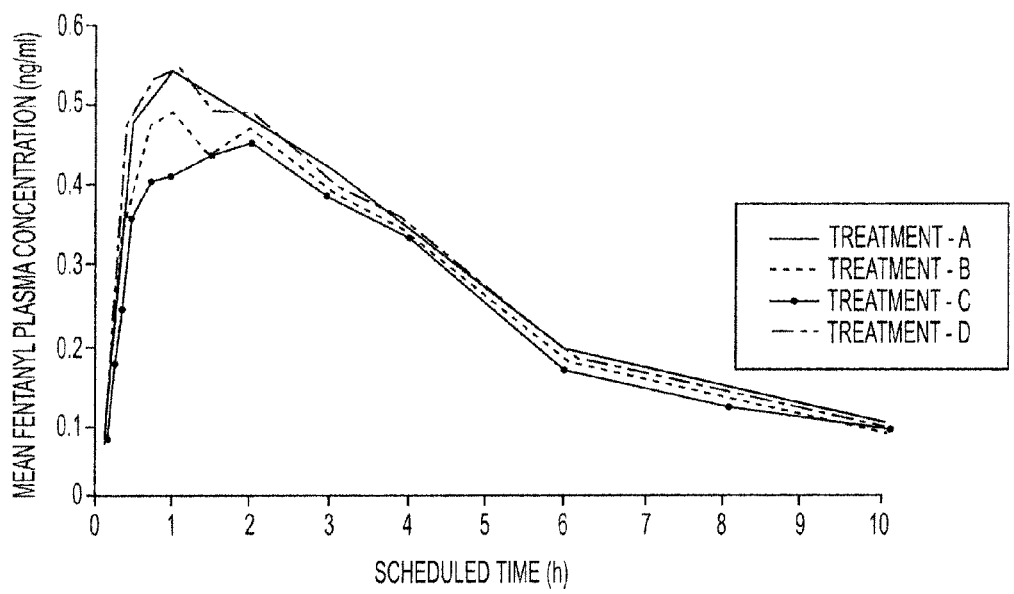
FIG. 2 is an illustration the plasma concentration-time profiles of fentanyl administered in compositions according to the invention during a clinical study described in Example 9.

Mean fentanyl plasma concentrations are presented by treatment in FIG. 2.

In the foregoing specification, the present invention has been described with reference to various examples and preferred embodiments. However, for a person skilled in the art, it is clear that the scope of the invention is not limited to these examples and embodiments, and that further modifications and variations are possible without departing from the inventive idea. The scope of the invention is thus only limited by the appended claims.

We claim:

1. A method comprising sublingual administration to an individual of a pharmaceutical composition in the form of a tablet sized for placement under a tongue, wherein the composition comprises:
(a) water-soluble carrier particles having exterior surfaces;
(b) microparticles of at least one pharmaceutically active agent selected from the group consisting of diazepam, oxazepam, zopiclone, zolpidem, propiomazine, valeriana, levomepromazin, and pharmaceutically acceptable salts thereof, wherein said microparticles are smaller than the carrier particles and are admixed with the carrier particles, and
(c) particles of a bioadhesion and/or mucoadhesion promoting agent consisting essentially of a polymer that swells when brought into contact with saliva admixed with the carrier particles,
wherein the microparticles of the at least one pharmaceutically active agent are presented at the exterior surfaces of the carrier particles.

2. A method according to claim 1 wherein the pharmaceutically active agent is zolpidem, or a pharmaceutically acceptable salt thereof.

3. A method comprising sublingual administration of at least one dosage unit of an essentially water free pharmaceutical composition to an individual, said pharmaceutical composition comprising an effective amount of at least one pharmaceutically active agent selected from the group consisting of diazepam, oxazepam, zopiclone, zolpidem, propiomazine, valeriana, levomepromazin, and pharmaceutically acceptable salts thereof, in the form of microparticles adhered to the surfaces of carrier particles which are substantially larger than said microparticles and are essentially water-soluble, and a bioadhesion and/or mucoadhesion promoting agent.

4. A method according to claim 3, wherein the pharmaceutically active agent is zolpidem, or a pharmaceutically acceptable salt thereof.

* * * * *